US012622599B2

(12) United States Patent
Alshehri et al.

(10) Patent No.: US 12,622,599 B2
(45) Date of Patent: May 12, 2026

(54) SAMPLE COLLECTION METHODS AND APPARATUS FOR VIRAL LOAD LEVEL DIAGNOSIS

(71) Applicant: The Regents of the University of California, Oakland, CA (US)

(72) Inventors: Ali Alshehri, Los Angeles, CA (US); Hossein Kavehpour, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 790 days.

(21) Appl. No.: 18/046,680

(22) Filed: Oct. 14, 2022

(65) Prior Publication Data

US 2023/0136493 A1     May 4, 2023

Related U.S. Application Data

(63) Continuation of application No. PCT/US2021/027456, filed on Apr. 15, 2021.

(Continued)

(51) Int. Cl.
*G01N 33/497*         (2006.01)
*A61B 5/08*           (2006.01)
*G01N 33/569*         (2006.01)

(52) U.S. Cl.
CPC ....... *A61B 5/082* (2013.01); *G01N 33/56983* (2013.01)

(58) Field of Classification Search
CPC .................................................. G01N 33/497
See application file for complete search history.

(56) References Cited

U.S. PATENT DOCUMENTS 1,625,821 A     4/1927  Pabodie
4,619,269 A *  10/1986  Cutler ................... A61B 5/083
                                                        128/205.12
(Continued)

FOREIGN PATENT DOCUMENTS

EP           1292225 B1     8/2005
JP           3744987 B2     2/2006
(Continued)

OTHER PUBLICATIONS

Arabi et al., "Performance evaluation of desalination processes based on the humidification/dehumidification cycle with different carrier gases," Desalination, 156: 281-293 (2003).

(Continued)

*Primary Examiner* — John E Breene
*Assistant Examiner* — Alex T Devito
(74) *Attorney, Agent, or Firm* — Foley Hoag LLP; David P. Halstead; Erik A. Huestis

(57) ABSTRACT

Provided herein are apparatuses, systems, kits, and methods, for detecting a virus contained within human breath or ambient air. The apparatus includes a housing comprising a base and a cover, the base having a sample collection surface, and the cover having a port and substantially enclosing the sample collection surface thereby defining a sample collection chamber. The apparatus includes a tube extending through the port and configured to receive a gaseous sample containing moisture and direct the gaseous sample to the sample collection surface. The apparatus includes a cooling device configured to cool the gaseous sample and thereby condense the moisture on the sample collection surface and a sample collection material disposed on the sample collection surface. The sample collection material is configured to absorb the condensed moisture.

12 Claims, 13 Drawing Sheets

Related U.S. Application Data

(60) Provisional application No. 63/010,453, filed on Apr. 15, 2020.

(56) References Cited

U.S. PATENT DOCUMENTS

| | | | |
|---|---|---|---|
| 7,779,840 | B2 | 8/2010 | Acker et al. |
| 8,523,985 | B2 | 9/2013 | Govindan et al. |
| 9,320,984 | B2 | 4/2016 | Govindan et al. |
| 9,700,811 | B2 | 7/2017 | Govindan et al. |
| 9,968,281 | B2 | 5/2018 | Bulbrook |
| 10,286,335 | B2 | 5/2019 | Govindan et al. |
| 2005/0059086 | A1 | 3/2005 | Huang et al. |
| 2007/0004995 | A1 | 1/2007 | Horn et al. |
| 2010/0216175 | A1 | 8/2010 | Melker et al. |
| 2014/0024024 | A1 | 1/2014 | Sood et al. |
| 2015/0274805 | A1 | 10/2015 | Annabi et al. |
| 2020/0033323 | A1 | 1/2020 | Funch-Nielsen |

FOREIGN PATENT DOCUMENTS

| | | |
|---|---|---|
| JP | 4118325 B2 | 7/2008 |
| NL | 1006858 C2 | 3/1999 |
| WO | WO-2020/009798 A1 | 1/2020 |
| WO | WO-2021/211821 A2 | 10/2021 |
| WO | WO-2021/243035 A1 | 12/2021 |

OTHER PUBLICATIONS

Chafik., "Design of plants for solar desalination using the multi-stage heating/humidifying technique," Desalination, 168: 55-71 (2004).

Fabian et al., "Influenza virus in human exhaled breath: an observational study," PloS One, 3(7): e2691 (6 pages)(2008).

Horvath et al., "Exhaled breath condensate: methodological recommendations and unresolved questions," European Respiratory Journal, 26(3): 523-548 (2005).

International Search Report and Written Opinion for International Application No. PCT/US2021/027456 notification mailed Oct. 13, 2021.

International Search Report and Written Opinion for International Application No. PCT/US2021/034543 mailed Sep. 2, 2021.

Narayan et al., "Helium as a carrier gas in humidification dehumidification desalination systems," Proceedings of the ASME 2011 International Mechanical Engineering Congress Exposition: 8 pages (2011).

Narayan et al., "The potential of solar-driven humidification-dehumidification desalination for small-scale decentralized water production," Renewable and Sustainable Energy Reviews, 14: 1187-1201 (2010).

Nunn et al., "New regression equations for predicting peak expiratory flow in adults," BMJ, 298(6680): 1068-1070 (1989).

Othmer., "The condensation of steam," Industrial & Engineering Chemistry, 21: 576-583 (1929).

Rose., "Personal reflections on fifty years of condensation heat transfer research," Journal of Enhanced Heat Transfer, 22: 89-120 (2015).

Sadeghpour et al., "Water vapor capturing using an array of traveling liquid beads for desalination and water treatment," Science Advances, 5(4): eaav7662 (9 pages)(2019).

Tow et al., "Experiments and modeling of bubble column dehumidifier performance," International Journal of Thermal Science, 80: 65-75 (2014).

Xu et al., "Molecular and Microscopic Analysis of Bacteria and Viruses in Exhaled Breath Collected Using a Simple Impaction and Condensing Method," PLoS One, 7(7): e41137 (2012).

Yan et al., "Infectious virus in exhaled breath of symptomatic seasonal influenza cases from a college community," PNAS, 115(5): 1081-1086 (2018).

* cited by examiner

SAMPLE COLLECTION METHODS AND APPARATUS FOR VIRAL LOAD LEVEL DIAGNOSIS

CROSS-REFERENCE TO RELATED APPLICATION

This application is a Continuation of International Application PCT/US21/27456, filed on Apr. 15, 2021, which claims the benefit of U.S. Provisional Patent Application No. 63/010,453, filed on Apr. 15, 2020. Each of these applications are hereby incorporated by reference in its entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

The rapid spread and virulence of COVID-19 has exposed a critical need for both individual patient point of care and environmental sampling and testing. To protect society from the current wave of illnesses and the potential second (possibly deadlier wave), efficient sampling and rapid testing should be deployed into critical infrastructure including food processing plants, hospitals, dental offices, essential government offices, airports, etc. The following is a list of qualities of a testing system for a viral pathogen: (a) the test system should provide fast, efficient patient testing taking samples directly from the lungs where the virus is most abundant; (b) the test system should provide a non-invasive test since the high-volume testing will involve children, senior citizens, mental health patients, and many others who cannot tolerate swab tests; (c) swab tests are known to cause secondary infection for high percentage of the sampling cases. (d) the gold standard outcome of testing would be monitoring for both virus and antibodies on the same sampling; (e) health care providers need a way to monitor viral load in lungs directly to better understand when patients are no longer contagious to quickly gauge the efficacy of different treatments; (f) a system is needed for environmental monitoring to determine contamination in rooms and surfaces by continuously sampling the air and the aerosols that settle onto counters, floors and other horizontal surfaces; (g) a system is needed for providing data to understand amount of virus in exhaled breath to better understand necessary distancing and danger of infection in the absence of coughs and sneezes.

Current patient sampling is performed by deep nasal swabbing and there is no known system capable of sampling the environment for COVID-19. It has been shown that viruses can be retrieved from the exhaled breath, by analyzing HEPA filters described in "Influenza virus in human exhaled breath: an observational study" by Fabian, et al. Additionally, it has been shown that viruses can be retrieved from the exhaled breath, by analyzing an Exhaled Breath Condensation (EBC) technique described in "Infectious virus in exhaled breath of symptomatic seasonal influenza cases from a college community" by Yan, et al. Existing EBC may take 30 minutes to an hour of breathing through a tube in order to collect sufficient samples as described in "Exhaled breath condensate: methodological recommendations and unresolved questions." by Horvath et al.

BRIEF SUMMARY

In various embodiments, an apparatus includes a housing comprising a base and a cover. The base has a sample collection surface and the cover has a port and substantially encloses the sample collection surface thereby defining a sample collection chamber. The apparatus further includes a tube extending from a proximal end to a distal end, where the proximal end has a proximal opening and the distal end has a distal opening, and the tube extends through the port such that the distal opening is in fluid communication with the sample collection chamber. The proximal opening is configured to receive a gaseous sample containing moisture and direct the gaseous sample to the sample collection surface. The apparatus further includes a cooling device configured to cool the sample collection surface and thereby condense at least a portion of the moisture on the sample collection surface. The apparatus further includes a sample collection material disposed on the sample collection surface, and the sample collection material is configured to absorb the condensed moisture.

In various embodiments, a method for detecting a virus contained within breath of a human is provided where a gaseous sample of human breath containing moisture at a sample collection surface is received. The sample collection surface is cooled to a temperature lower than the dew point of the moisture in the gaseous sample thereby condensing the moisture on the sample collection surface. At least a portion of the condensed moisture is collected.

In various embodiments, a method for detecting a virus contained within ambient air is provided where a gaseous sample of ambient air containing moisture at a sample collection surface is received. The sample collection surface is cooled to a temperature lower than the dew point of the moisture in the gaseous sample thereby condensing the moisture on the sample collection surface. At least a portion of the condensed moisture is collected.

BRIEF DESCRIPTION OF THE SEVERAL VIEWS OF THE DRAWINGS

The objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

Figure 1:
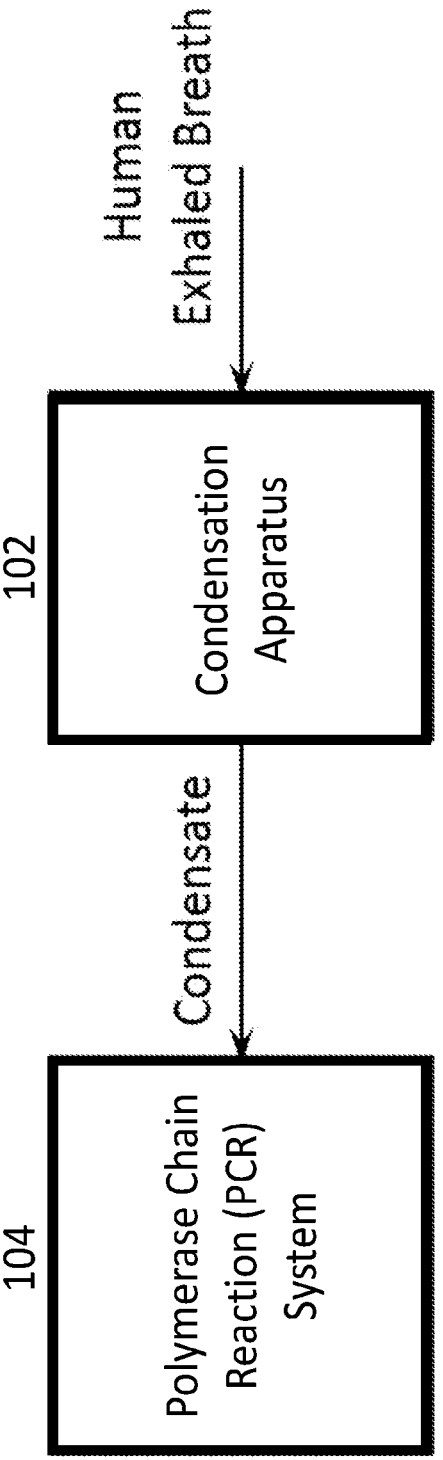
FIG. 1 illustrates a diagram showing a general method for collecting samples of condensed air moisture for polymerase chain reaction (PCR) analysis of virus presence in accordance with an embodiment of the present disclosure.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

This disclosure describes apparatuses, systems, kits, and methods for collecting samples of condensed air moisture for viral load level diagnosis. In various embodiments, samples can be collected from a patient in less than a minute. For example, humid air could be sampled from a patient's breath or from environmental (e.g., room) air. In various embodiments, the condensed moisture may be transported to, for example, a polymerase chain reaction (PCR) system for analysis of virus presence.

This disclosure also describes a condensation mechanism that has experimentally been found to be significantly more efficient than state-of-the art dehumidification systems. In one embodiment, the basic principle of the mechanism is to direct the patient's breath or humid air such that it impinges on a surface that is cooled down to a desired temperature lower than the dew point of the incoming air. For example, a patient could blow into a tube that directs the patient's breath toward the surface as one or more jet of air. In various embodiments, because the surface is cooled below the dew point of the incoming air, a breath figure (BF) spot appears very quickly (e.g., almost instantaneously). In various embodiments, this BF spot includes micron-sized water droplets. In various embodiments, as the user breathes through the tube and the droplets grow, the shearing effects of the jet act to push them radially outward to an equilibrium radial location. In various embodiments, the water droplets (that may contain a target, e.g., virus, bacteria, fungus, etc.) may be collected by, for example, either flushing the surface with a sterile liquid (e.g., sterile water) or using a wicking material to absorb the condensed droplets. In various embodiments, the liquid droplets can then be transported for analysis (e.g., PCR, immunofluorescence, staining, etc.).

This disclosure also describes an apparatus for carrying out the foregoing procedures. In various embodiments, the apparatus may include (a) a collection surface that optionally may be treated with a hydrophobic material, (b) a tube, which is preferably disposable, that directs a patient's exhaled breath to impinge on the collection surface, (c) means for cooling the collection surface (e.g., an thermoelectric or Peltier plate thermally coupled or pasted to the underside of the collection surface) to provide the cooling capacity required for condensation, (d) a cover or enclosure coupled to the tube and which forms a chamber to contain the exhaled breath within the apparatus (to be vented out appropriately), and (e) a sample collection mechanism. In one embodiment, the sample collection mechanism may comprise an elongated wick for absorbing the condensed droplets. In various embodiments, the collection mechanism could be a ring-shaped material located at the equilibrium radial location mentioned earlier. In other embodiments, the collection mechanism could be a wicking material, surface grooving/texturing, gravity-assisted, or external-flow assisted collection mechanism.

In various embodiments, the sampling apparatus described herein can provide low-cost monitoring system for point-of-care testing, with quick interfacing to analysis systems as well as environmental monitoring which are needed for re-opening public spaces, public safety, and protecting against the current and future pandemics.

Further aspects of the technology described herein will be brought out in the following portions of the specification, wherein the detailed description is for the purpose of fully disclosing preferred embodiments of the technology without placing limitations thereon.

In various embodiments, an apparatus is provided for collecting samples of condensed air moisture for viral load level diagnosis. FIG. 1 illustrates a flow diagram of an embodiment including a condensation apparatus 102 and a polymerase chain reaction (PCR) system 104. In various embodiments, humid air may be sampled from a patient's breath or from environmental (e.g., room) air by the condensation apparatus 102, such as the apparatuses described herein. In various embodiments, the condensed moisture collected by the condensation apparatus 102 may be transported to the PCR system 104 for analysis of virus presence. In various embodiments, the PCR system may be any suitable commercially-available PCR system (e.g., qPCR).

Figure 2:
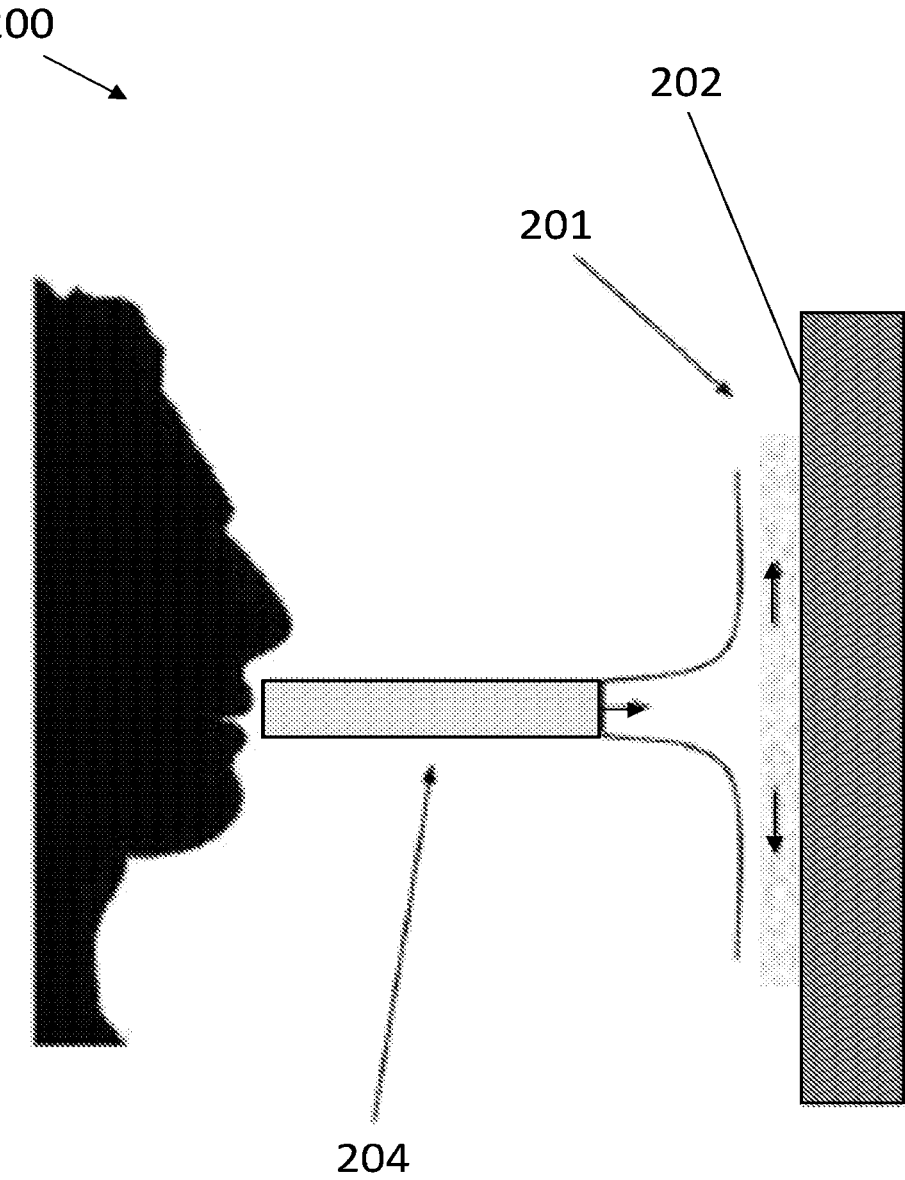
FIG. 2 illustrates a schematic diagram illustrating sample collection in accordance with an embodiment of the present disclosure.

In various embodiments, the condensation apparatus 102 described herein has been experimentally found to be more efficient than state-of-the art dehumidification systems with respect to collecting moisture from a human breath and/or the ambient air. Referring to FIG. 2, in various embodiments, the apparatus 200 directs a gaseous sample containing moisture (e.g., a patient's breath or humid air) such that the gaseous sample impinges on a sample collection surface 202 (of a sample collection base 201) that is cooled down to a desired temperature that is lower than the dew point of the incoming air. In various embodiments, a patient may blow into a tube 204 (e.g., disposable tube) that is configured to direct and focus the patient's breath as a jet of air toward the sample collection surface 202. In various embodiments, because the sample collection surface 202 (i.e., the surface facing the user) is cooled below the dew point of the incoming air, a breath figure (BF) spot appears quickly (e.g., almost instantaneously). In various embodiments, this BF spot may include one or more micron-sized water droplets. In various embodiments, as the droplets grow, shearing effects of the jet passing over the droplets pushes the droplets radially outward to an equilibrium radial location. In various embodiments, these water droplets (containing the target, e.g., virus, bacteria, fungus, etc.) may be collected by either flushing the surface with water or using a wicking material to absorb the condensed droplets. In various embodiments, a ring shaped collection material may be placed at or near this equilibrium radial location. In various embodiments, a ring shaped collection material may be placed at a radius that is less than the equilibrium radial location to thereby collect additional droplets. In various embodiments, the liquid droplets can then be transported for analysis.

Figure 3:
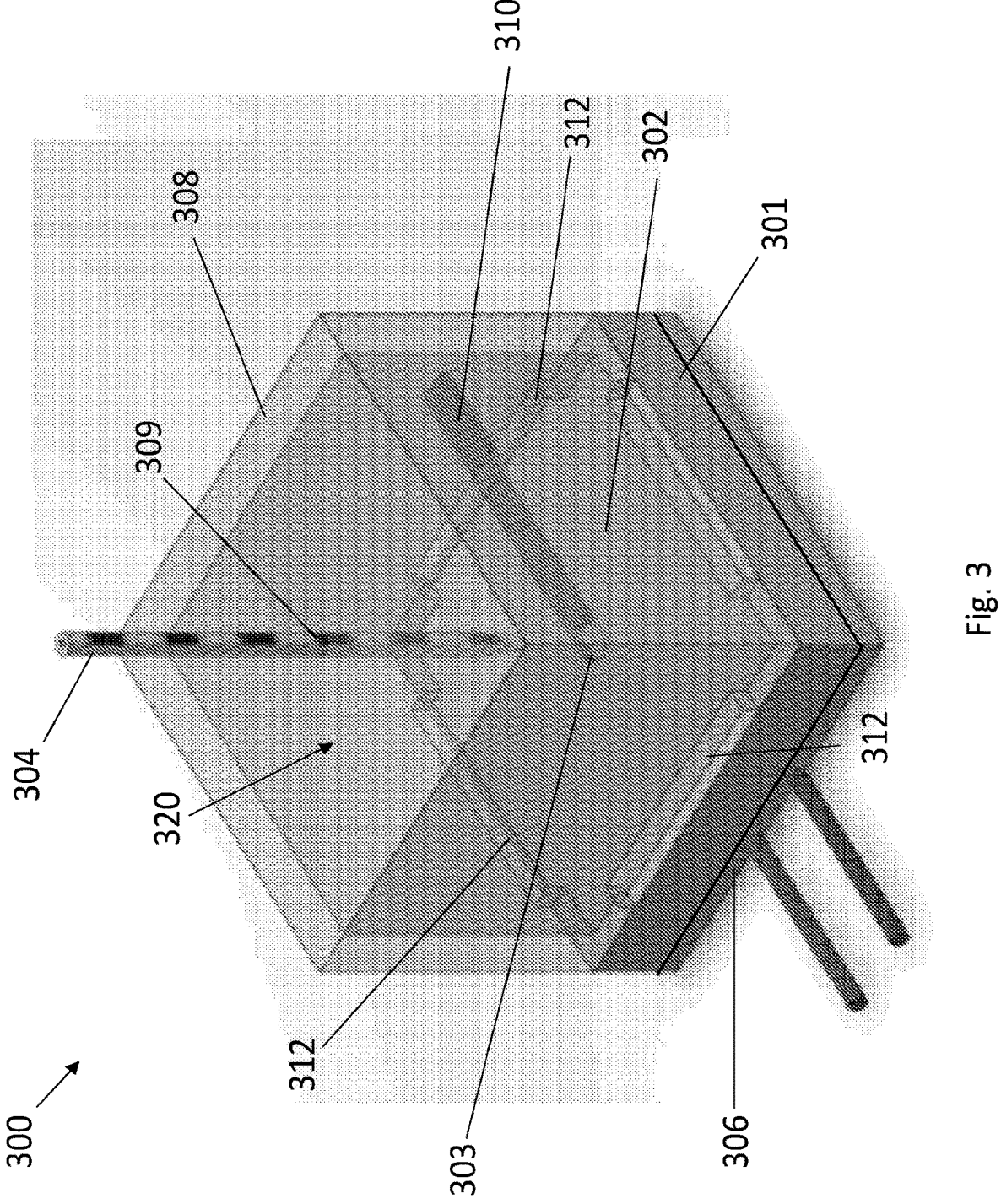
FIG. 3 illustrates an assembled view of a sample collection apparatus in accordance with an embodiment of the present disclosure.
Figure 4:
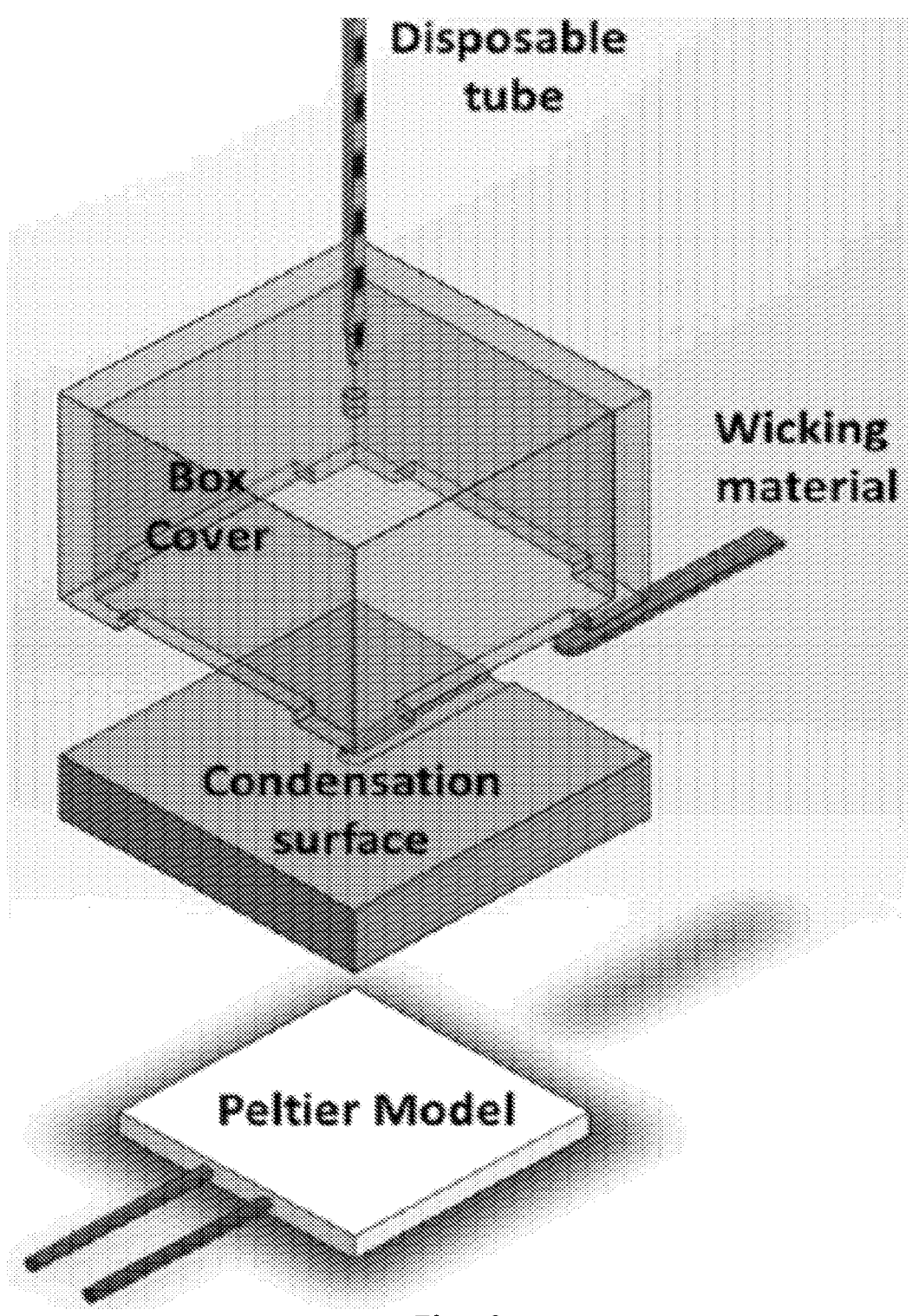
FIG. 4 illustrates an exploded view of the apparatus of FIG. 3 in accordance with an embodiment of the present disclosure.
Figure 5:
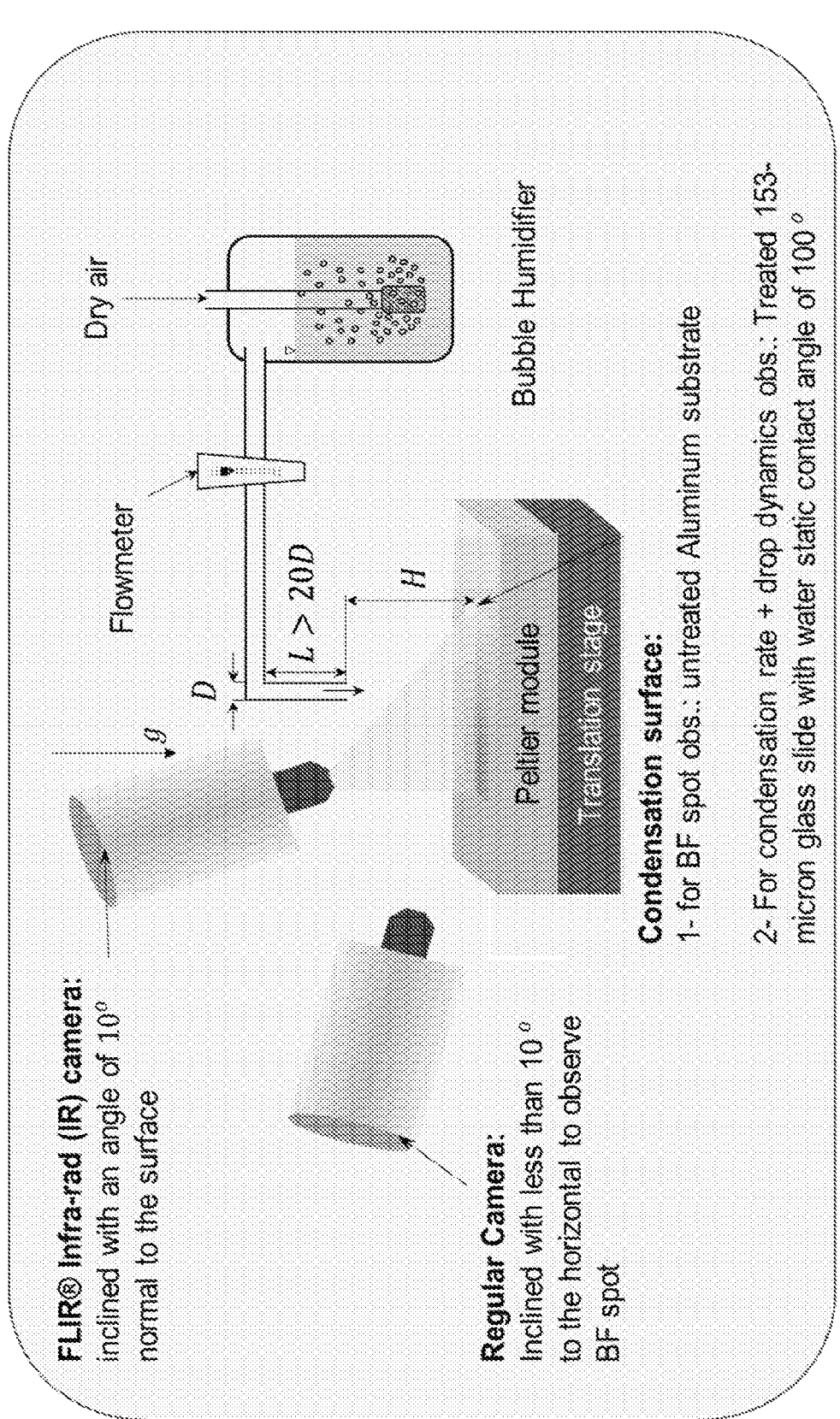
FIG. 5 illustrates an experimental setup used for condensate extraction from a humid air jet in accordance with an embodiment of the present disclosure.

FIG. 3 illustrates an assembled sample collection apparatus 300 and FIG. 4 illustrates an exploded view of the sample collection apparatus 300 according to the present disclosure. In various embodiments, the apparatus comprises (a) a sample collection surface 302 (of a sample collection base 301) that may be optionally treated with hydrophobic material, (b) a tube 304, which is preferably disposable, configured to direct a patient's exhaled breath thereby impinging the focused jet of breath on the collection surface, (c) a cooling device 306 that cools the collection surface with sufficient cooling capacity to form condensation, (d) a cover 308 or enclosure coupled to the tube 304 and which forms a chamber to contain the exhaled breath within the apparatus (to be vented out appropriately), and (e) a sample collection material 310 disposed within a slot 303 (e.g., a trough). In various embodiments, the sample collection base 301 and the cover 308 collectively form a housing that is substantially enclosed (e.g., except for the port and vents).

In the embodiment illustrated in FIG. 3 and FIG. 4, the cover 308 fits over the sample collection surface 302 to form a sample collection chamber 320 having a substantially-enclosed volume. In various embodiments, the cover 308 has at least one inlet port 309 through which the distal end of the tube 304 may be inserted to provide fluid communication between a proximal end of the tube 304 and the substantially-enclosed chamber. In various embodiments, the tube 304 extends through the port such that a distal opening of the tube 304 is in fluid communication with the sample collection chamber 320. Preferably, the cover has a single inlet port 309. In various embodiments, the at least one inlet port 309 may be position substantially at the center of the cover. In various embodiments, the inlet port 309 may be positioned relative to collection material (e.g., wicking material) such that the droplets are absorbed by the collection material. In various embodiments, the inlet port 309 may be positioned directly over the sample collection material 310, such as in the embodiment where the sample collection material 310 is linear in shape. In other embodiments, the inlet port 309 may be positioned at the center of the sample collection material 310, such as in the embodiment where the sample collection material 310 is ring-shaped.

In various embodiments, the base 301 (including the sample collection surface 302) of the sample collection chamber 320 may be cooled via a cooling device 306. In various embodiments, the cooling device 306 may be a thermoelectric device beneath the base 301 of the sample collection chamber 320. In various embodiments, the cooling device 306 may be a Peltier plate thermally coupled (e.g., thermally pasted) to the underside of the base 301 of the sample collection chamber 320. Other suitable methods known in the art could be used as well, provided that the cooling capacity is sufficient to form condensation from the gaseous sample. In various embodiments, any suitable cooled solid, liquid, gas, and/or combination of phases could be used as a cooling device. For example, ice (H$_2$O), dry (CO$_2$) ice, or liquid nitrogen could be placed in contact with the base 301 to thereby cool the base such that condensation will form as the gaseous sample is received in the sample collection chamber 320.

In various embodiments, the sample collection surface 302 may include one or more slot 303 (e.g., a trough). In various embodiments, the slot 303 may extend at least partially along a length (e.g., length, width, diameter, etc.) of the sample collection surface 302. In various embodiments, the slot 303 may have a depth that is less than the thickness of the sample collection base 301. In various embodiments, the slot 303 may have a constant depth. In various embodiments, the slot 303 may have a varying depth. In various embodiments, the slot 303 may be cylindrically-shaped (e.g., a half cylinder). In various embodiments, the slot 303 may be positioned at a middle point of an edge of the sample collection surface 302. In various embodiments, the slot 303 may extend at least half of the length of the sample collection surface 302. In various embodiments, the slot 303 may be sized to optimize collection of condensed water droplets. In various embodiments, the slot 303 may include a ring shape (e.g., a ring-shaped trough).

In various embodiments, the sample collection surface 302 may include two or more slots 303. In various embodiments, any (e.g., all) of the two or more slots 303 may be configured to receive a sample collection material 310. In various embodiments, any slot(s) may be roughened (e.g., sand blasted) to improve retention of the sample collection material 310. In various embodiments, any (e.g., all) of the two or more slots 303 may be configured to collect droplets without a collection material disposed therein. For example, the sample collection surface 302 may include a slot disposed at two or more sides of the sample collection surface 302 (e.g., a slot 303 at the center of each edge, a slot 303 at each corner, two or more slots 303 disposed equiangularly about a circumference of a circular surface). In various embodiments, the two or more slots 303 may not meet with one another (i.e., each slot is distinct from one another). In various embodiments, any of the two or more slots 303 (e.g., all) may meet at a predetermined location along the surface to thereby form an integral slot.

In various embodiments, the sample collection base 301 may include a funnel-shape that is configured to direct any resulting condensation down a drain. In various embodiments, the sample collection material 310 may be positioned in the drain (e.g., at the bottom of the drain).

In various embodiments, the sample collection material 310 may include a wicking material to absorb the condensed droplets. In various embodiments, the sample collection material 310 may include a ring-shaped material. In various embodiments, at least a portion (e.g., all) of the sample collection material 310 may be located at the equilibrium radial location on the sample collection surface 302. In various embodiments, a wicking material may be positioned in the slot 303 for absorbing the condensed droplets. In various embodiments, the wicking material may be, for example, a stiff material or be a covering over a support structure such as a swab body or wood stick type support structure. In various embodiments, the collection material 310 may include a ring-shaped material located at the equilibrium radial location as described above. In various embodiments, the collection mechanism may include a wicking material (e.g., cotton), surface grooving/texturing, gravity-assisted, or external-flow assisted collection mechanism. In various embodiments, the wicking material may be integrated into a card such that the card can be inserted into the slot 303 while the card collects condensed water droplets and removed once a suitable amount of condensed water droplets are collected.

In various embodiments, the sample collection surface 302 may be treated with receptors to one or more portions of a virus (e.g., virus coat protein, virus spike protein, etc.), such as for the COVID-19 virus. In various embodiments, after exposure to exhaled air or ambient air, the sample collection surface 302 may be placed into a processor where the unoccupied receptors can be illuminated fluorescently with known immunohistochemical methods. In various embodiments, the virus may be labelled with anti-virus (e.g., anti-COVID-19) antibodies, producing a direct readout of virus titer. In various embodiments, a direct testing "lab-on-a-chip" system may be provided.

In various embodiments, the cover 308 may include one or more vents 312. In various embodiments, the one or more vents 312 may be disposed such that one vent is on each side of the cover 308. In various embodiments, the one or more vents 312 may be equally-spaced around the cover 308. In various embodiments, the one or more vents 312 may be cutouts in the cover 308 that, when the cover 308 meets the sample collection surface 302, the vents 312 form slots configured to provide fluid communication between the chamber 320 and the ambient air and allow for outflow of the gaseous sample during use. In various embodiments, the one or more vents 312 may be rectangular cutouts. In various embodiments, the one or more vents 312 may be circular cutouts. In various embodiments, the one or more vents 312 may be square cutouts. In various embodiments, the one or more vents 312 may be oval cutouts. In various embodiments, the one or more vents 312 may have any suitable shape to provide for outflow of the gaseous sample. In various embodiments, each of the one or more vent may be a cutout along a bottom surface of the cover, such that the portions of the bottom surface that are not cutout are configured to contact the sample collection surface.

In various embodiments, a diameter of the tube 304 may be about 1 mm to about 5 mm. In various embodiments, the diameter of the tube 304 may be about 2 mm to about 3 mm. In various embodiments, a height between the distal end of the tube 304 and the sample collection surface 302 may be about 1 mm to about 200 mm. In various embodiments, the height between the distal end of the tube 304 and the sample collection surface 302 may be about 1 mm to about 100 mm. In various embodiments, the height between the distal end of the tube 304 and the sample collection surface 302 may be about 1.5 mm to 52.5 mm. In various embodiments, the flow rate of the gaseous sample (e.g., humid air) through the tube 304 may be about 0.5 liter per minute (LPM) to about 5 LPM. In various embodiments, the flow rate of the gaseous sample (e.g., humid air) through the tube 304 may be about 1 LPM to about 3 LPM. In various embodiments, a surface temperature of the sample collection surface 302 may be about 0° C. to about 22° C. In various embodiments, a surface temperature of the sample collection surface 302 may be about 22° C. to a temperature of 5° C.

It will be appreciated that the presented technology can be used in connection with detection of a variety of different viruses, bacteria, etc. and/or antibodies for diseases.

In various embodiments, the apparatus described herein may be used in any suitable type of airflow for sample collection, with two main applications related to current pandemic being human sampling and using natural ambient airflow to provide long term monitoring of important enclosed environments such as hospital, offices, schools, airport terminals, etc.

Example 1 (Experimental Procedure)

Figure 6:
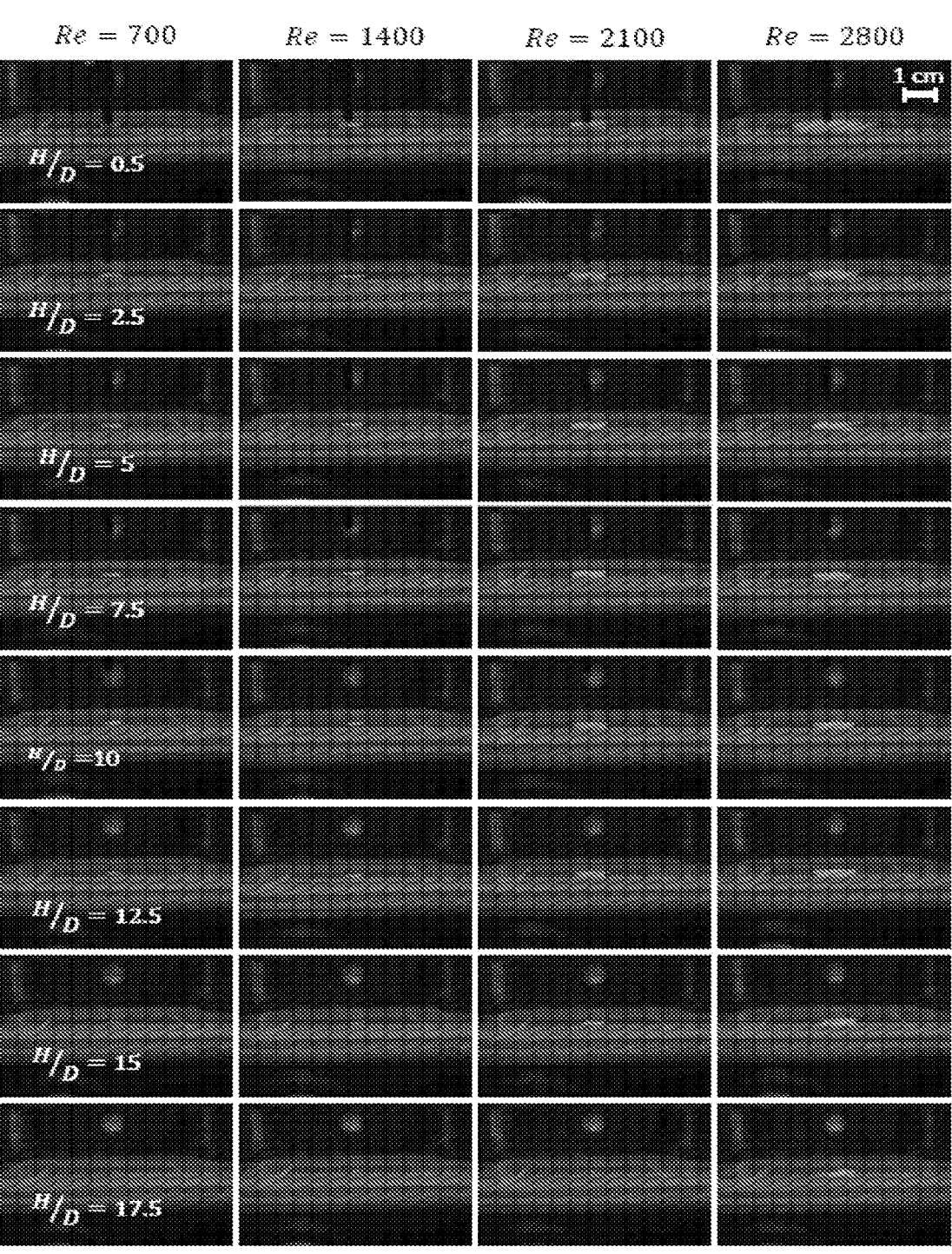
FIG. 6 illustrates regular camera photographs of the breath figures at varying heights-to-diameter ratios and jet Reynolds numbers in accordance with an embodiment of the present disclosure.

FIG. 6 shows the BF spots as photographed from a side view using a regular camera. In various embodiments, BF spots may appear cloudy because micron-sized droplets scatter light in all directions. This enables easier visualization of the spots and better quantification of BF spot behavior. In various embodiments, height and Reynolds number may have minimal effects on the extent to which BF spots expand. In the tested range, BF spots varied from one to ten tube diameters.

Figure 7:
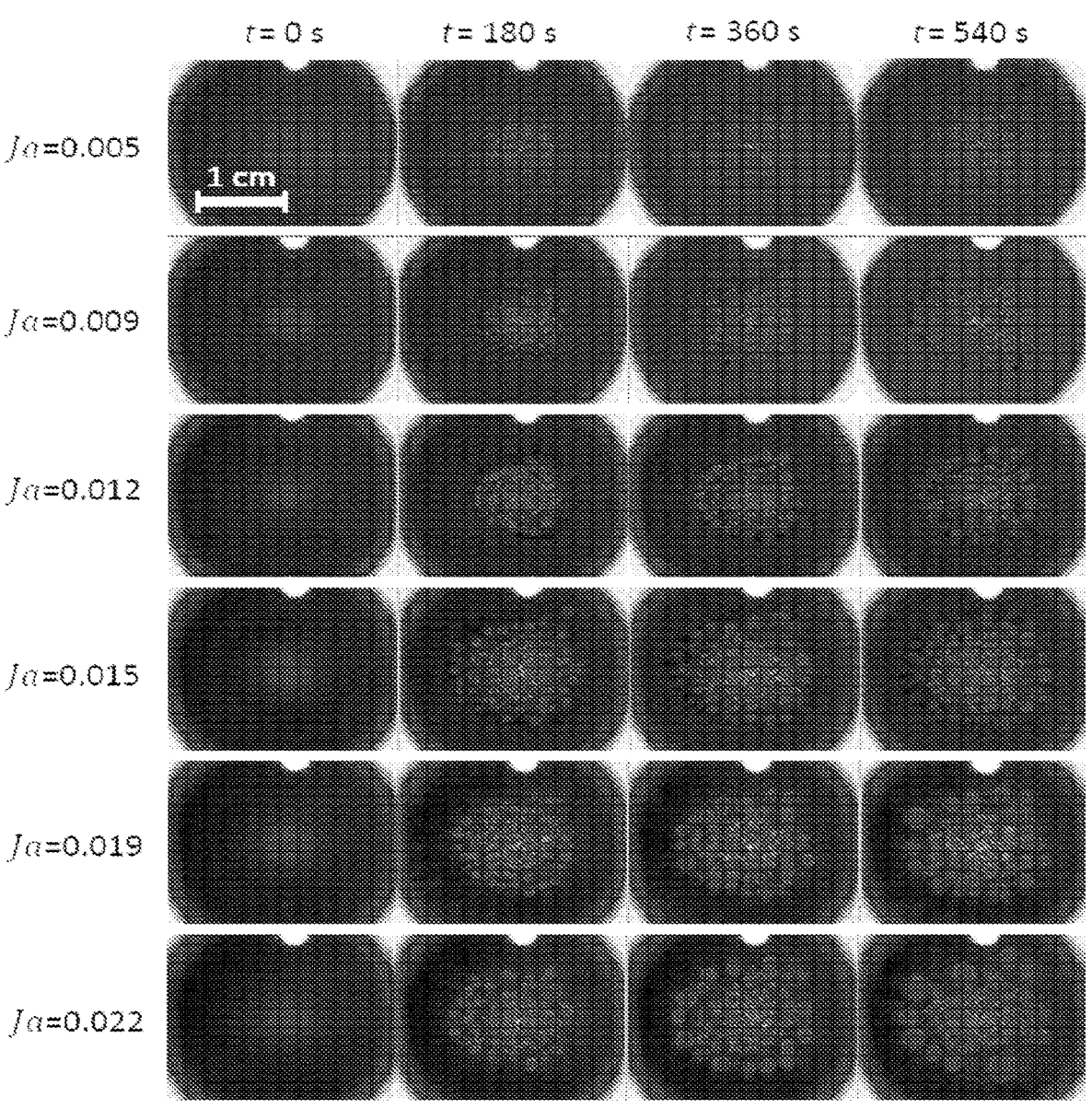
FIG. 7 illustrates an infrared camera pictures of droplet formation at different surface temperature and different times in accordance with an embodiment of the present disclosure.

FIG. 7 shows infrared (IR) camera snap shots of selected cases at different surface temperatures. As shown in FIG. 7, at the lower the surface temperature, the higher water droplet are collected. Additionally, for a given surface temperature, the water collected increases with time. As droplets grow, the shearing effects of the jet may push the droplets radially outward to an equilibrium location at which they could be collected. In various embodiments, the radial equilibrium location may be controlled by using different surface wettability coatings. In various embodiments, the surface wettability coating may include a hydrophobic silicon polymer (e.g., hydroxy-terminated polydimethylsiloxane).

Example 4 (Numerical Example)

In various embodiments, the sample collection apparatus may be design such that a person with a limited lung capacity could exhale sufficient water vapor to collect a sample in under a minute. For example, consider a person exhaling (temperature $T_j=35°$ C. and relative humidity $\varnothing_j=100\%$) through a tube of diameter (D=2 mm) onto a surface that is cooled to a temperature of ($T_s=5°$ C.). Based on experimental measurements, the mass transfer coefficient was found to be ($h_m A=0.0166$ g/s) if the breath flow rate is (Q=3 LPM). The mass flow rate for these settings is:

$$\dot{m}= \bar{h}_m A(\omega_\infty - \omega_s) = 1.32 \times 10^3 (1.26 - 10^{-5})(0.0353 - 0.0054) \approx 5 \times 10^{-4} \text{ g/s}$$

Figure 8:
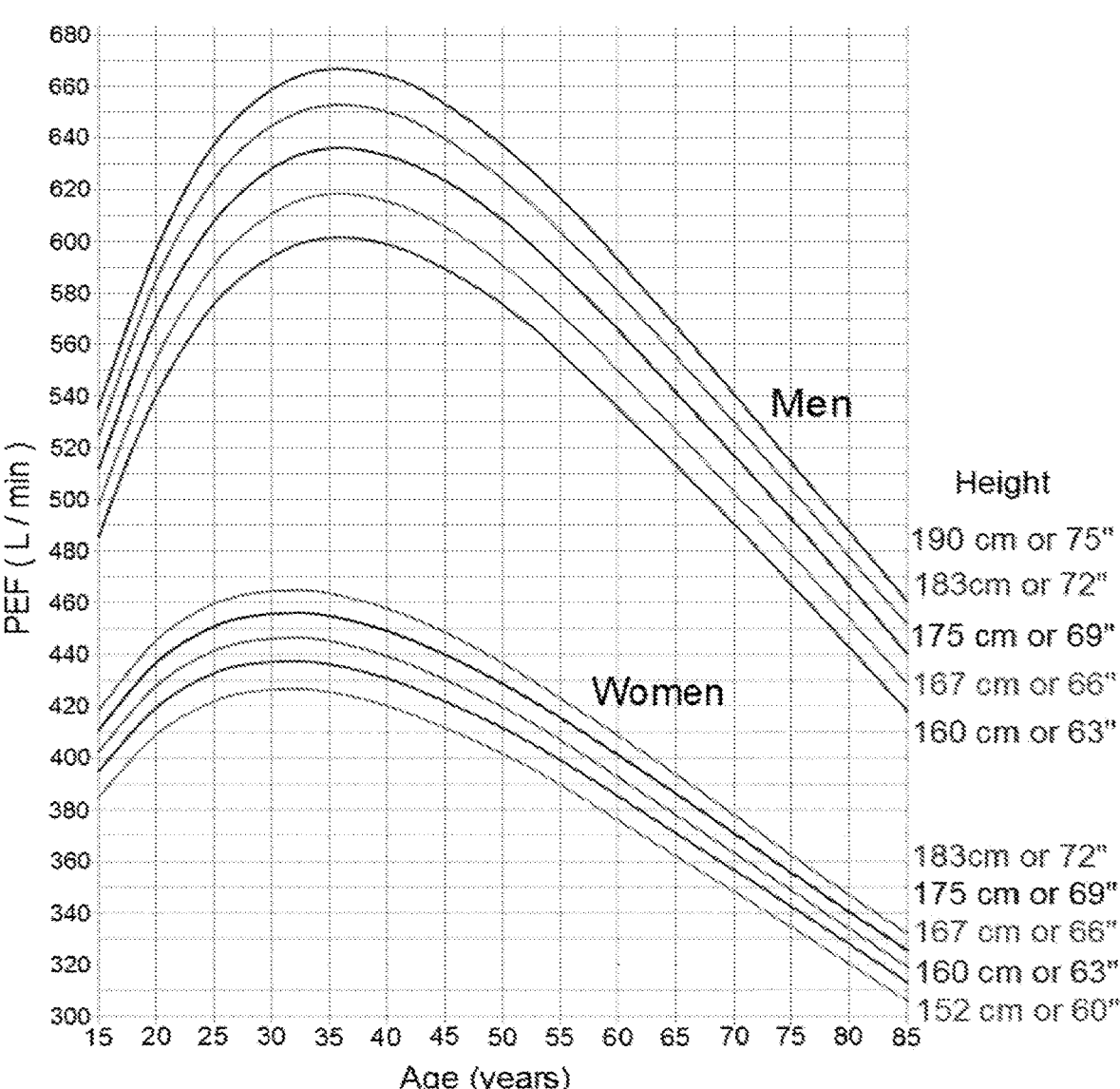
FIG. 8 illustrates a graph showing examples of human expiratory flow rate in accordance with an embodiment of the present disclosure.

If one exhales for 1 minute, around 0.03 cc of liquid may be collected. Referring to FIG. 8, in various embodiments, human expiratory flow rates can reach around 300 LPM. In various embodiments, a condensation rate of 2 mL/min is sufficient for diagnostic testing.

As described above, this disclosure provides for a highly efficient sample collection system, based on a novel condensation approach, that can convert humidified air from patient exhalation or directly from the local environment into a highly concentrated sample from which the virus titer can be extracted.

In various embodiments, the system is more efficient, and potentially up to 100× more efficient, at collection than any other Exhaled Breath Condensation (EBC) technique currently available giving us the potential to make rapid point of care collection and diagnosis more reliable. While existing EBC techniques can take 30 minutes to an hour of breathing through a tube in order to collect sufficient samples, in various embodiments, the presented technology can provide results in less than a minute.

In various embodiments, the presented collection system can easily and seamlessly be integrated into number of different detection systems including PCR and possibly future microfluidic platforms in a safe, clean and reusable way without cross-contamination between uses.

Figure 9:
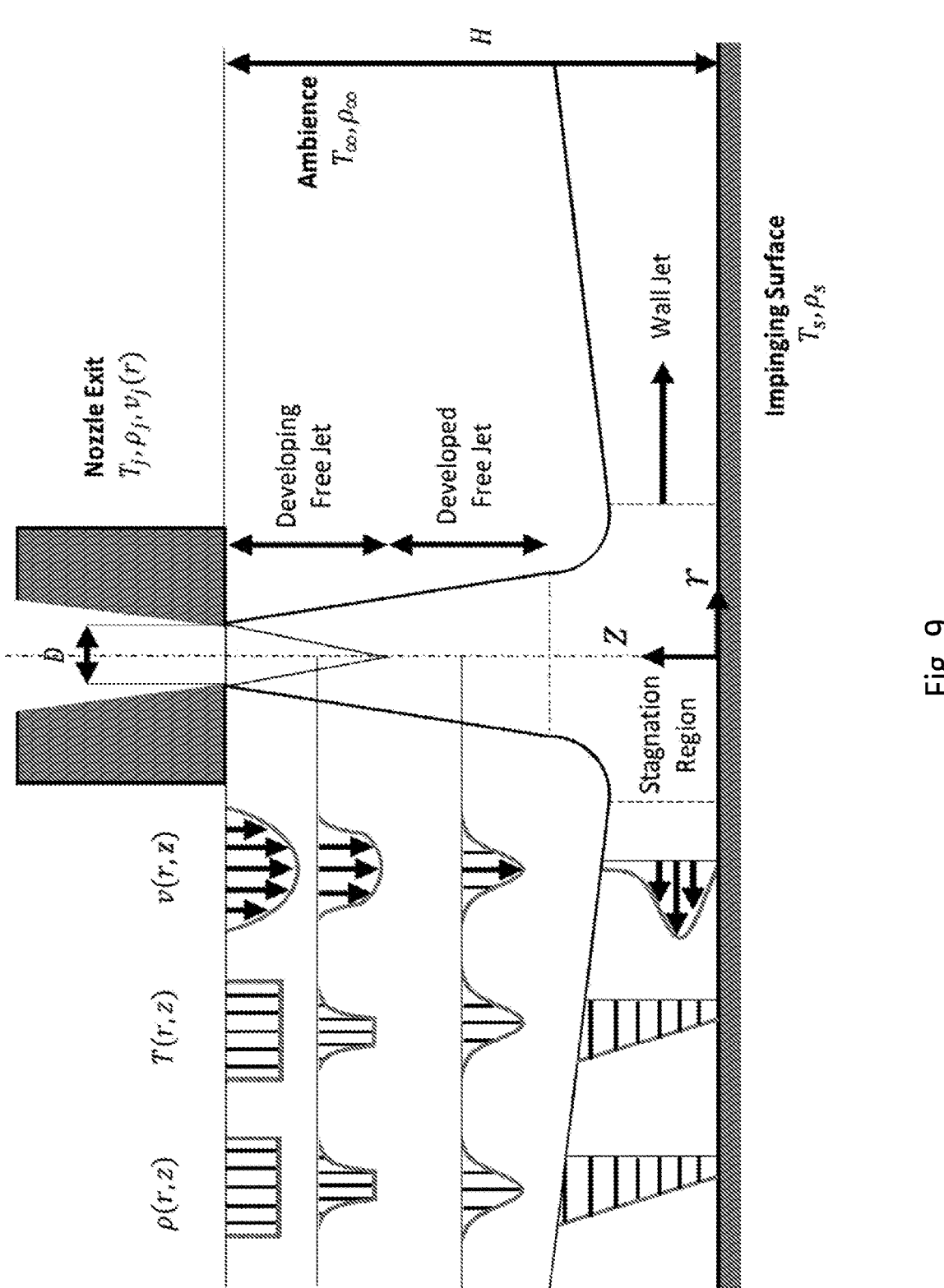
FIG. 9 illustrates a diagram of humid-air jet impingement in accordance with an embodiment of the present disclosure.

FIG. 9 shows a configuration of a jet exiting a nozzle and impinging on a surface in a quiescent ambience. In various embodiments, the jet may be submerged or non-submerged depending on whether the ambience is of similar density to the jet fluid. In various embodiments, the jet can be divided into three regions; (1) Free jet region, (2) stagnation/impingement region, and (3) wall jet region. In various embodiments, in the free jet region, flow, thermal, and species fields may not be affected by the solid wall downstream. Therefore, the variation of the state variables of this region can be matched with a free unbounded jet. In various embodiments, the free jet can be divided further into developing and developed regions, similar to that in pipe flow. In various embodiments, the developing region is characterized by a potential core that maintains the velocity profile of the nozzle exit. In various embodiments, momentum, heat, and mass are exchanged with the surroundings. In various embodiments, state variable variation may have a smooth transition. In various embodiments, this region may extend to almost five nozzle diameters. In various embodiments, in the developed region, the potential core may vanish, and the center line magnitude of state variables may start changing. In various embodiments, in the stagnation region, the speed of the jet may drop to zero at the center of the impingement area and the pressure may build up to a maximum of $(\rho v^2/2)$. In various embodiments, heat and mass transfer rates in the stagnation area may be significantly higher. In various embodiments, in the wall jet region, a regular boundary layer problem may be solved with prior knowledge of the boundary conditions. In various embodiments, several empirical correlations may be obtained under different conditions of single-phase heating or cooling applications. In various embodiments, a heat/mass transfer analogy may be utilized as well for drying processes. In various embodiments, in nucleate boiling, jet impingement may be observed and models may be used to estimate the boiling curve for such cases.

Many cases in single-phase jet impingement include a condition of a turbulent nozzle exit, which assumes a uniform velocity profile at the nozzle exit. Some reviewers have addressed most of physical phenomena and empirical correlations of gas jet impingement on solid surfaces, while other reviewers have focused on liquid jet impingement heat transfer. A major difference between gas and liquid jet impingement is the existence of a hydraulic jump in the latter case. In various embodiments, heat transfer by jet impingement may be affected by several parameters. In various embodiments, nozzle configuration, nozzle diameter, nozzle-to-surface spacing, jet velocity, and the mismatch between jet and ambient temperature and concentration may affect the impingement.

In various embodiments, the nozzle geometrical configuration may include shapes, such as Square-edged orifices, standard-edged orifices, and sharp-edged orifices. In various embodiments, the nozzle may include round nozzles, e.g., round nozzles with arrays of triangular tabs. In various embodiments, the nozzles may be round, square, and/or rectangular nozzles. In various embodiments, the nozzle configurations may be an important factor for enhancing the turbulent mixing of the jet. In various embodiments, turbulent mixing acts to enhance the heat transfer significantly. In various embodiments, comparison with fully-developed pipe jet impingement may show improvement as high as 55% in stagnation region heat transfer. In various embodiments, improvements as high as 75% may be achieved by replacing contoured nozzles with orifice nozzles. In various embodiments, round nozzles may produce the least pressure drops compared to square or rectangular nozzles. In various embodiments, length scales may be normalized by the nozzle diameter (or radius). In various embodiments, length scales may be normalized in the free jet region, the stagnation region, and/or wall jet regions. In various embodiments, the height-to-diameter ratio (H/D) may affect some variables. In various embodiments, for a uniform nozzle exit velocity, the Nusselt number radial distribution may function in two ways. For heights higher than five nozzle diameters, the distribution may be characterized by a bellshaped curve for which Nu monotonically drops from the stagnation point outward. For lower heights, there exists a secondary peak in Nusselt number distribution that may exceed the stagnation point peak. In various embodiments, a height value of five diameters may correspond to the end of the developing free jet and start of a developed one.

Figure 10A:
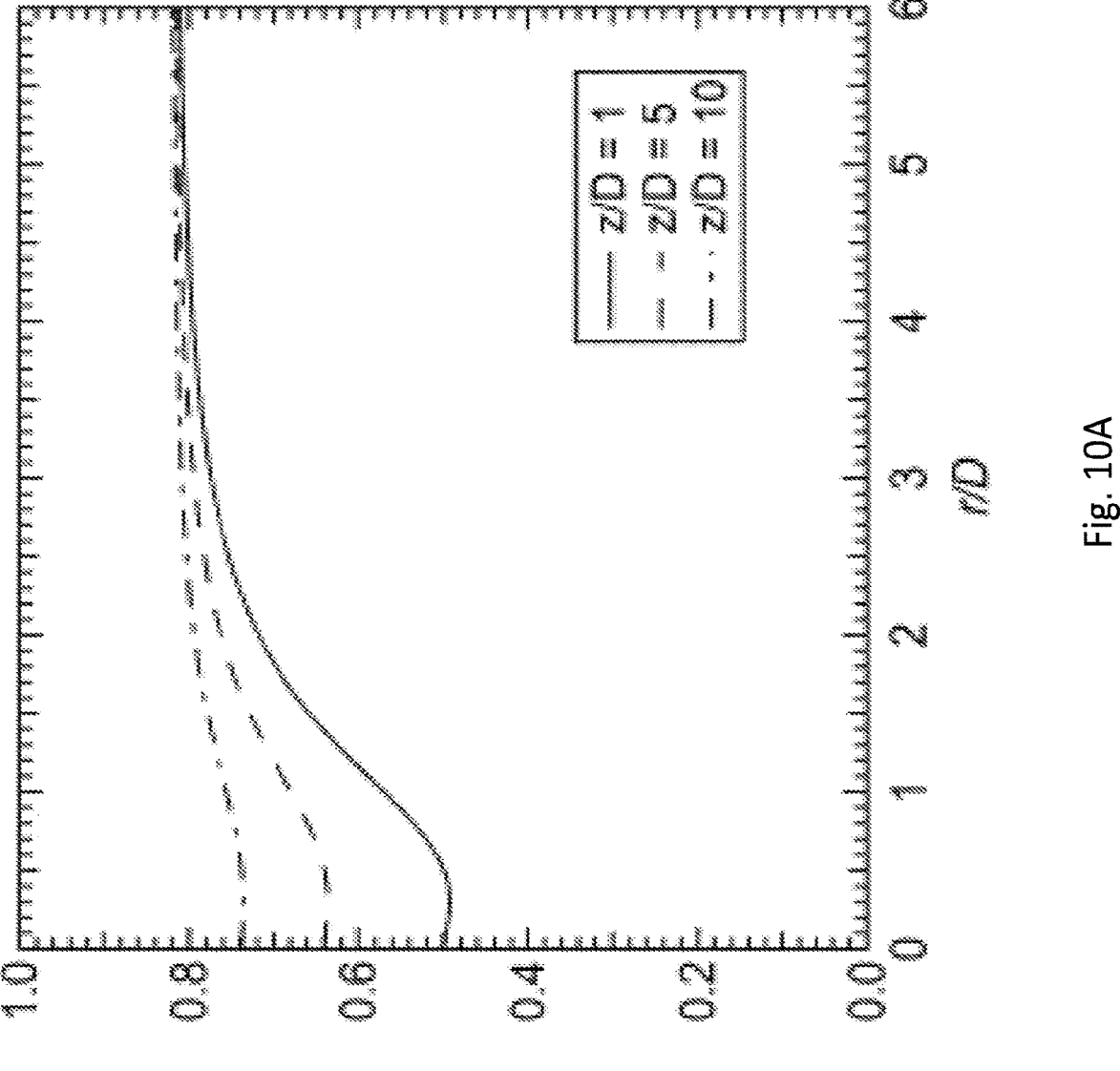
FIGS. 10A-10B illustrate graphical correlation of the power law constants K and a at various conditions for local Nusselt number in accordance with an embodiment of the present disclosure.
Figure 10B:
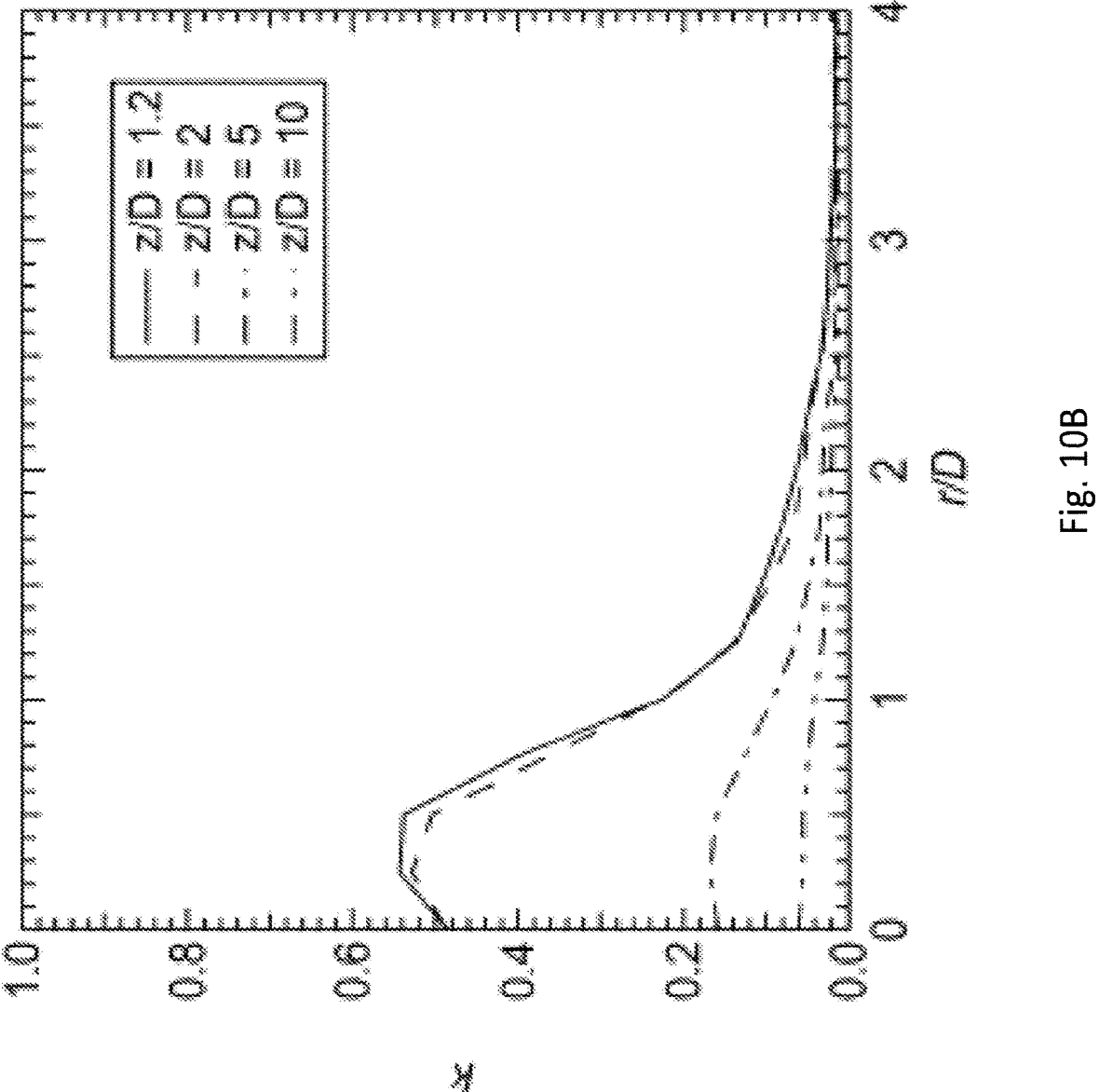

In various embodiments, the effect of jet velocity may vary based on at least one of: the combination of height-to-diameter ratio, radial location and Reynolds number. In various embodiments, a power law of the local Nusselt number may be defined in an equation as follows:

$$Nu = kRe^\alpha \qquad \text{(Eqn. 1)}$$

where k and a are constants that depend on height-to-diameter ratio and radial location. In various embodiments, an empirical correlation of these constants may be obtained by experimental work. FIGS. 10A-10B show a graphical correlation of both k and a at various conditions. In various embodiments, the results may be obtained for a turbulent jet with Reynolds number ranging from 5,000 to 124,000. In various embodiments, for Jet Reynolds number of 2,000 to 400,000 and height-to-diameter ratio range of 2 to 12, average Nusselt number in radial locations from 2.5 to 7.9 nozzle diameters are found using the following equation:

$$\frac{\overline{Nu}}{Pr^{0.42}Re^{0.5}} = \frac{2 - 2.2(D/r)}{(r/D) + 0.1(H/D - 6)}(1 + 0.005Re^{0.55})^{1/2} \qquad \text{(Eqn. 2)}$$

In various embodiments, the problem of mismatch between jet and ambient temperature or concentration may be solved by introducing a recovery (or an adiabatic wall) temperature. In various embodiments, correlations of local heat transfer coefficients may be developed based on the difference between recovery temperature and the surface temperature. In various embodiments, the recovery temperature may take into account the entrainment resulting from the diffusive exchange between the jet and the ambience.

In various embodiments, the term two-phase flow may includes but not limited to cases where a phase change takes place. In various embodiments, in jet impingement, applications that can be described as two phase flows include: drying, spray/mist cooling, and/or nucleate boiling.

Drying using jet impingement has been used in food industry, textile industry and other applications. In various embodiments, for moderate evaporation rate cases, a heat and mass transfer analogy may be sufficient to predict mass transfer rates from heat transfer ones. In various embodiments Nusselt number may be predicted from Sherwood number using the following analogy equation:

$$\frac{\overline{Nu}}{Pr^{0.42}} = \frac{\overline{Sh}}{Pr^{0.42}} \qquad \text{(Eqn. 3)}$$

In various embodiments, Eqns. 1 and 2 can be used for both Nusselt and Sherwood numbers interchangeably. In various embodiments, this application of Eqns. 1 and 2 may be valid if the heat and mass transfer are decoupled. In various embodiments, such in the case of high evaporation rates or higher density variations, a deviation from the heat and mass transfer analogy may occur.

In various embodiments, another application where jet impingement is considered is in flow boiling. In various embodiments, because in the developing nucleate boiling regime both convective and nucleation heat transfer rates are high, heat transfer rates may be significant compared to pool boiling cases. In various embodiments, in free jet impingement boiling, a saturated or subcooled liquid jet is impinged on a heated surface in a quiescent gas surrounding, while a submerged jet may be characterized by similar jet and surrounding liquids. In various embodiments, in the case of free jets, the jet parameters, such as jet velocity, diameter and subcooling may not be involved in the fully developed nucleate boiling regime. In various embodiments, the effects of such parameters is clear in the single-phase region, developing nucleate boiling region, onset of nucleate boiling (ONB), and critical heat flux (CHF). In various embodiments, correlations may be developed to estimate the complete boiling curve. In various embodiments, as for submerged jet impingement boiling, the jet parameters may affect the fully developed nucleate boiling region. In various embodiments, the effect of the surrounding subcooling may influence the entire process. In various embodiments, another factor influencing jet impingement boiling may include surface condition. In various embodiments, even though single-phase region is not influence by the surface wettability, it is a highly controlling parameter in all the other regions. In various embodiments, lower surface wettability enhances the bubble generation and departure. In various embodiments, lower surface wettability enhances the mixing mechanism that is essential in nucleate boiling. In various embodiments, some experiments were performed on highly conductive heaters, hence constant surface superheat. In addition, heater dimension may be similar to the jet dimension which in turn limits the cases to the stagnation region. In various embodiments, the heater area is greater than the jet diameter. In various embodiments, for lower conductive heaters or heaters with large areas, the heater are appropriately described in constant heat flux terms. In various embodiments, this may result in a variation of the surface temperature in the radial direction with the lowest temperature being at center of the stagnation area. In various embodiments, single phase region, developing and developed nucleate boiling could be observed simultaneously from the center of the stagnation region and radially outward, in the same order. In various embodiments, the ONB may be formed in a shape of a ring with a stable reproducible size.

In various embodiments, researchers have considered numerically studying such behavior. In various embodiments, numerous numerical models may include Eulerian mixture models, Eulerian mechanistic model, and/or single-phase model. In various embodiments, the Eulerian mixture models are based on numerically solving for the state variables in the vapor and liquid domains separately. In various embodiments, empirical relations were used for the evaporation rates for inter-phase mass transfer. In various embodiments, forces on bubbles were performed by simple drag force and surface tension balance. In various embodiments, the interface heat transfer was set to be infinite therefore constant temperature can be employed at the interface of the two phases. In various embodiments, the Eulerian mechanistic model is similar to that developed for pool boiling. The general form of the mechanistic model is $$q''_w = q''_{convective} + q''_{quenching} + q''_{evaporative} \qquad \text{(Eqn. 3)}$$

or $$q''_w = \qquad \text{(Eqn. 3)}$$

-continued $$h(1-A_b)(T_w-T_l)+\frac{2}{\sqrt{\pi}}A_b\sqrt{f\rho_l k_l c_{p,l}}\,(T_w-T_l)+\frac{\pi}{6}D^2 fN\rho_v h_{fg}$$

In various embodiments, in the fully developed nucleate boiling region, the evaporative heat flux may be neglected. In various embodiments, by knowing the bubble departure diameter (D), departure frequency (f), bubble covered area ratio ($A_b$), and nucleation site density (N), the wall heat flux may be predicted. In various embodiments, because of the negligible effect of evaporative heat flux, and the fact that heat transfer is enhanced by the mixing phenomenon caused by bubble departure, the single-phase model may be more appealing. In various embodiments, a modification made to normally solving for state variables is an additional artificial turbulent diffusivity. In various embodiments, jet impingement may be used in spray or mist cooling technology. In various embodiments, in the case of spray cooling, micro jets may be sprayed directly on a hot surfaces. In various embodiments, high temperature steam may be expanded abruptly and therefore, condensate droplets are generated and impinged on a hot surface in mist cooling. In various embodiments, evaporative cooling is the main mechanism by which heat is removed from the surface.

In various embodiments, a jet impingement technique may be used to study droplet growth mechanisms on hydrophobic surfaces. In various embodiments, oblique jets may be utilized where the jet is not normal to the surface to reduce its shearing effect. In various embodiments, oblique jets may be used for better visualization of the transient droplet growth. In various embodiments, a solution to a sudden NCG leakage in a pure vapor condensation heat exchanger may include generating a jet of pure steam and impinging the inner tube to breath the diffusion layer. In various embodiments, improvements may be obtained of around two fold compared to the absence of the jet.

Figure 11:
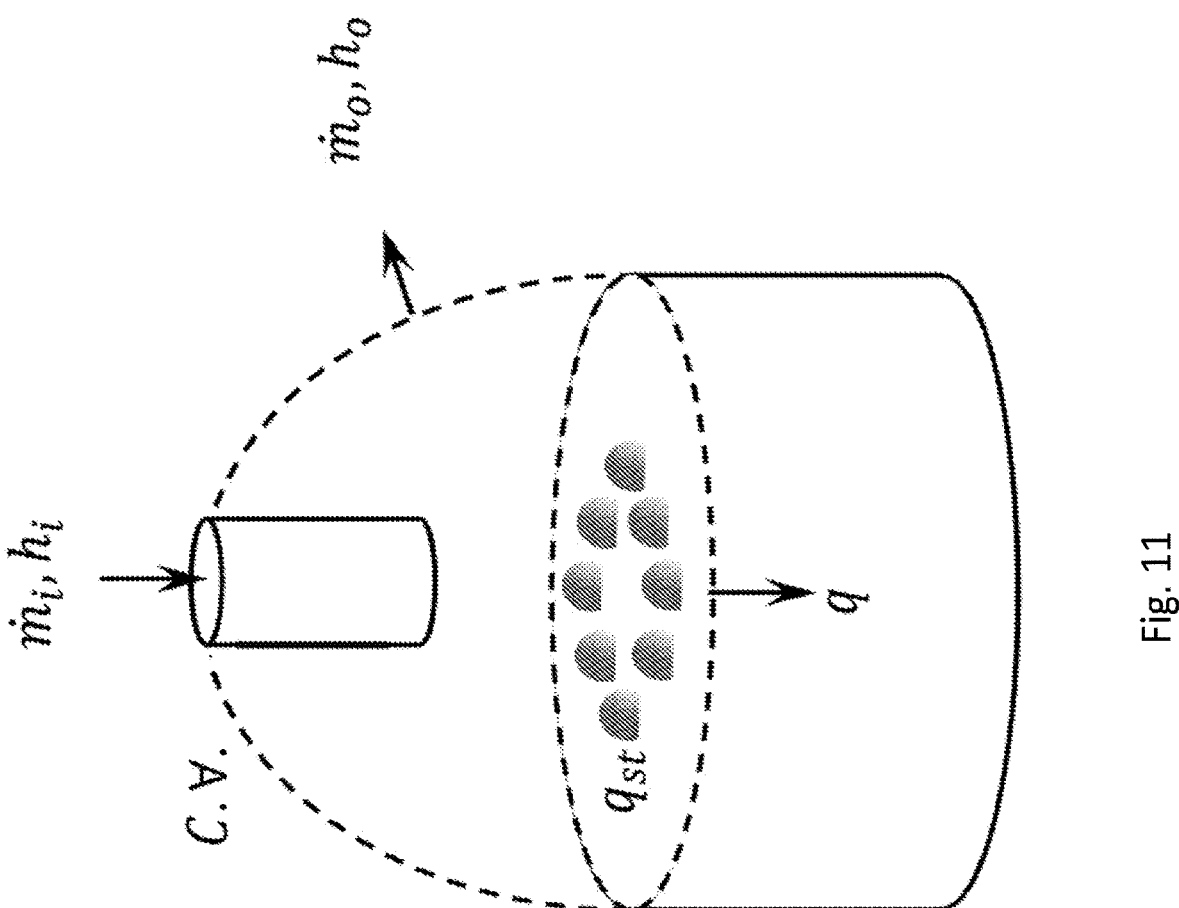
FIG. 11 illustrates a control volume (CV) on which thermodynamic analysis may be performed in accordance with an embodiment of the present disclosure.

FIG. 11 illustrates a control volume (CV) over which thermodynamic analysis may be performed. In various embodiments, humid air enters the CV at a temperature equivalent to room temperature (T1) and relative humidity of (RH1). In various embodiments, the contained water vapor is dehumidified by impingement on a surface at a temperature lower than the dew point. The dehumidified air then leaves the CV with a minute change to its overall mass flow rate. In various embodiments, the condensation process is represented as an energy stored in the system. Because the condensation latent heat ($h_{fg}\sim2.447\times10^6$) is two orders of magnitude higher than sensible heat ($c_p\Delta T_{max}\sim1.8\times10^4$), the latter can be neglected. Therefore, utilizing the concluded condensation rate in the previous section, the heat transfer rate is found as:

$$q''=\dot{m}''_c h_{fg} \tag{Eqn. 4}$$

Consequently, the overall heat transfer coefficient is obtained as:

$$\overline{U}=\frac{q''}{(T_j-T_{RTD})}=\frac{k\overline{Nu}}{d} \tag{Eqn. 5}$$

In traditional heat/mass exchangers, the compactness of such machines may be calculated as the ratio between their surface area to their occupied volume which is sometimes referred to as area density. However, this definition lacks an important parameter which is the heat/mass transfer coefficient. Because heat/mass exchanger compactness is a design coefficient to be maximized, the following definition may be more suitable instead of area density:

$$C_m=\frac{\dot{m}''A}{\Delta\omega\overline{V}}=\frac{h_m A}{\overline{V}} \tag{Eqn. 6}$$

$$C_H=\frac{q''A}{\Delta T\overline{V}}=\frac{\overline{U}A}{\overline{V}} \tag{Eqn. 7}$$

In this case, the heat/mass exchanger system can be estimated to be that of a cylindrical shape. In various embodiments, the base area may be used for normalizing the condensation rate. The height of the cylinder is the nozzle-to-surface spacing (H). In various embodiments, the area density may reduce to (1/H).

Figure 12:
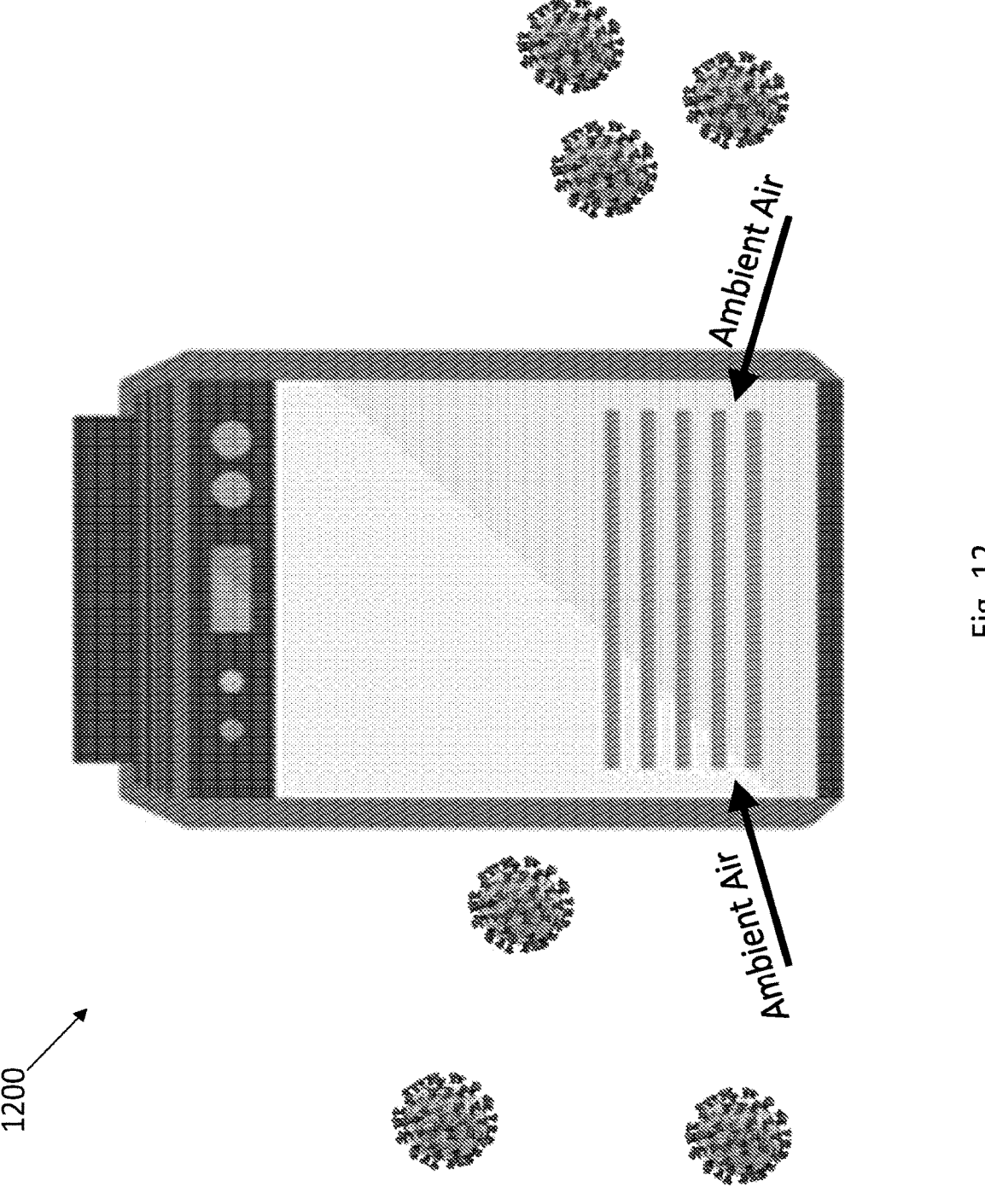
FIG. 12 illustrates an exemplary system for detecting viral presence in accordance with an embodiment of the present disclosure.

FIG. 12 illustrates an exemplary system 1000 for detecting viral presence in accordance with an embodiment of the present disclosure. As shown in FIG. 12, the system 1200 may include a dehumidification device and/or an air purifier device. In various embodiments, the system 1200 may force ambient air into a sample collection chamber via one or more fans. In various embodiments, the system 1200 may passively receive ambient air.

In various embodiments, the system 1000 may include an integral UV light. In various embodiments, the system 1000 may include a camera system (e.g., digital camera) for detecting fluorescence (and/or lack thereof). In various embodiments, the system may include an enzyme-linked immunosorbent assay (ELISA). In various embodiments, the system 1000 may include a rapid antigen test (e.g., an immunochromatographic/lateral flow assay). In various embodiments, as virus in ambient air lands on a chip, the virus may bind to an antibody coating on the sample collection surface. In various embodiments, the bound virus may inactivate a fluorophore (such that the camera would be looking for an absence of fluorescence). In various embodiments, after a predetermined limit of virus is determined, the system 1000 may provide an indication to a user (e.g., throw an alarm, illuminate a light, etc.). In various embodiments, a user may insert/remove a consumable lab-on-a-chip into the system 1000.

In various embodiments, a user may remove the collection material for testing (e.g., at a PCR machine or enzyme-linked immunosorbent assay). In various embodiments, a user may remove the collection material for testing via an antigen test (e.g., lateral flow) used to test for virus presence. In various embodiments, after the collection material has been removed, new collection material may be inserted to replace the spent collection material.

In various embodiments, a sample collection apparatus for viral load level diagnosis is provided. The apparatus comprises: (a) a sample collection surface; (b) a cover configured to enclose the sample collection surface and thereby form a sample collection chamber; (c) a tube having a proximal opening and a distal opening, the distal opening in communication with the sample collection chamber, the proximal opening configured to receive a gaseous sample containing moisture and direct the gaseous sample to impinge on the sample collection surface; (d) a cooling device configured to provide sufficient cooling to condense moisture in the gaseous sample that impinges on the collection surface; and (e) a sample collection material configured to absorb condensed moisture.

The apparatus of any preceding or following embodiment, wherein the collection surface is treated with a hydrophobic material. The apparatus of any preceding or following embodiment, wherein the tube is disposable. The apparatus of any preceding or following embodiment, wherein the cooling device comprises a thermoelectric device. The apparatus of any preceding or following embodiment, wherein the thermoelectric device is thermally coupled to the sample collection surface. The apparatus of any preceding or following embodiment, wherein the collection surface is treated with a receptor to a virus coat protein. The apparatus of any preceding or following embodiment, wherein the virus is the COVID-19 virus. The apparatus of any preceding or following embodiment, wherein the apparatus is a component of an "on chip" testing system wherein unoccupied receptors can be illuminated fluorescently with standard immunohistochemical methods and/or the virus itself could be labelled with anti-virus antibodies, producing a direct readout of virus titer.

In various embodiments, a method for collecting a sample for viral load level diagnosis is provided. The method comprising: (a) directing an gaseous sample containing moisture toward a sample collection surface; (b) cooling the sample collection surface to a temperature lower than the dew point of the moisture in the gaseous sample; (c) wherein moisture in the gaseous sample that impinges on the sample collection surface forms condensation on the sample collection surface; and (d) collecting at least a portion of the condensation for diagnosis.

The method of any preceding or following embodiment: wherein the sample collection surface is covered by a cover that encloses the sample collection surface and thereby forms a sample collection chamber; wherein the gaseous sample is directed to the sample collection surface using a tube having a proximal opening configured to receive the gaseous sample and a distal opening configured to direct the gaseous sample into the sample collection chamber for impingement on the sample collection surface; wherein the sample collection surface is cooled using a device configured to provide sufficient cooling to condense moisture in the gaseous sample that impinges on the collection surface; and collecting the at least a portion of the condensation for diagnosis using a material configured to absorb condensed moisture. The method of any preceding or following embodiment, wherein the collection surface is treated with a hydrophobic material. The method of any preceding or following embodiment, wherein the tube is disposable. The method of any preceding or following embodiment, wherein the cooling device comprises a thermoelectric device. The method of any preceding or following embodiment, wherein the thermoelectric device is thermally coupled to the sample collection surface. The method of any preceding or following embodiment, wherein the collection surface is treated with a receptor to a virus coat protein. The method of any preceding or following embodiment, wherein the virus is the COVID-19 virus. The method of any preceding or following embodiment, further comprising illuminating unoccupied receptors fluorescently with standard immunohistochemical methods and/or labeling the virus itself with anti-virus antibodies, producing a direct readout of virus titer.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus comprising:
a housing comprising a base and a cover, the base having a sample collection surface, the cover having a port and at least one vent disposed on each side of the cover, the cover substantially enclosing the sample collection surface thereby defining a sample collection chamber;
a tube extending from a proximal end to a distal end, the proximal end having a proximal opening and the distal end having a distal opening, the tube extending through the port such that the distal opening is in fluid communication with the sample collection chamber, wherein the proximal opening is configured to receive a gaseous sample containing moisture and direct the gaseous sample to the sample collection surface;
a cooling device configured to cool the sample collection surface and thereby condense at least a portion of the moisture on the sample collection surface; and
a sample collection material disposed on the sample collection surface, the sample collection material configured to absorb the condensed moisture.

2. The apparatus of claim 1, wherein each vent comprises a cutout along a bottom surface of the cover, wherein at least a portion of the bottom surface is configured to contact the sample collection surface.

3. The apparatus of claim 1, wherein the sample collection material comprises a ring, wherein the ring is positioned on the sample collection surface such that the tube is directed at a center of the ring.

4. The apparatus of claim 1, wherein the sample collection surface comprises a slot, wherein the slot comprises a depth that is less than a thickness of the base and wherein the base comprises a first length and the slot comprises a second length, wherein the second length is less than the first length.

5. The apparatus of claim 4, wherein the sample collection material is disposed in the slot.

6. The apparatus of claim 1, wherein the sample collection surface comprises a hydrophobic treatment, wherein the hydrophobic treatment comprises a hydrophobic silicon polymer.

7. The apparatus of claim 1, wherein the tube is removable from the port.

8. The apparatus of claim 1, wherein the cooling device comprises a thermoelectric device, wherein the cooling device is thermally coupled to the sample collection surface and wherein the cooling device is configured to cool the sample collection surface to between about 5° C. and about 22° C.

9. The apparatus of claim 1, wherein the sample collection surface comprises a receptor to a coat protein of a virus.

10. The apparatus of claim 1, wherein the sample collection material comprises a wicking material and one or more antibodies.

11. The apparatus of claim 1, wherein the sample collection surface comprises one or more antibodies.

12. The apparatus of claim 1, wherein a height between the distal end of the tube and the sample collection surface is about 1.5 mm to about 52.5 mm and wherein a diameter of the tube is about 2 mm to about 3 mm.

* * * * *